(12) United States Patent
Raulerson et al.

(10) Patent No.: US 11,701,141 B2
(45) Date of Patent: *Jul. 18, 2023

(54) OCCLUDABLE INTRODUCER NEEDLE

(71) Applicant: Medical Components, Inc., Harleysville, PA (US)

(72) Inventors: J. Daniel Raulerson, Brewton, AL (US); Mark S. Fisher, Sellersville, PA (US)

(73) Assignee: J Daniel Raulerson, Brewton, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/449,221

(22) Filed: Sep. 28, 2021

(65) Prior Publication Data

US 2022/0008097 A1 Jan. 13, 2022

Related U.S. Application Data

(63) Continuation of application No. 16/452,657, filed on Jun. 26, 2019, now Pat. No. 11,134,980, which is a continuation of application No. 14/978,304, filed on Dec. 22, 2015, now Pat. No. 10,383,656.

(60) Provisional application No. 62/096,628, filed on Dec. 23, 2014.

(51) Int. Cl.
*A61B 17/34* (2006.01)
*A61M 25/06* (2006.01)
*A61M 25/09* (2006.01)
*A61M 25/00* (2006.01)

(52) U.S. Cl.
CPC .............. *A61B 17/34* (2013.01); *A61M 25/06* (2013.01); *A61M 25/0097* (2013.01); *A61M 25/09041* (2013.01)

(58) Field of Classification Search
CPC .............. A61B 17/34; A61M 25/0612; A61M 25/0606; A61M 25/0097; A61M 25/09041; A61M 25/06; A61M 25/0014; A61M 25/0693; A61M 39/0606; A61M 39/26; A61M 39/0693; A61M 39/281; A61M 39/28; A61M 39/283; A61M 39/284; A61M 39/285; A61M 39/286; A61M 39/287; A61M 39/288; A61M 2025/09116; A61M 5/32; F16K 7/00; F16K 7/07; F16K 7/075; F16K 7/08; F16K 7/10
See application file for complete search history.

(56) References Cited

U.S. PATENT DOCUMENTS

| | | |
|---|---|---|
| 5,263,938 A | 11/1993 | Orr et al. |
| 5,489,274 A | 2/1996 | Chu et al. |
| 2005/0043684 A1 | 2/2005 | Basta et al. |
| 2010/0030160 A1 | 2/2010 | Glocker |

(Continued)

*Primary Examiner* — Emily L Schmidt
*Assistant Examiner* — Alexandra Lalonde

(57) ABSTRACT

An introducer needle assembly including a compressible section between a rigid needle and a hub. Once a vessel is entered as determined by blood entering a syringe, the compressible section of the introducer needle is occluded by compressing the compressible section with a thumb and a finger. Neither blood nor air can pass. Since the compressible section is in a flattened area it is easier to hold the needle while the syringe is unscrewed. An operator then can begin threading a guidewire down a divide which is now easier to enter because blood is not coming out of the hub thus obscuring a lumen.

18 Claims, 3 Drawing Sheets

(56) References Cited

U.S. PATENT DOCUMENTS

2014/0203555 A1* 7/2014 Frankland ............ A61M 25/09
285/390
2015/0045771 A1 2/2015 Hayakawa et al.

* cited by examiner

OCCLUDABLE INTRODUCER NEEDLE

CROSS-REFERENCE TO RELATED APPLICATIONS

This application is a continuation of U.S. patent application Ser. No. 16/452,657, filed Jun. 26, 2019, which is a continuation of U.S. patent application Ser. No. 14/978,304, filed Dec. 22, 2015, which claims the benefit of U.S. Provisional Application No. 62/096,628, filed on Dec. 24, 2014, the contents of each of which are incorporated herein by reference as if repeated in entirety herewith.

FIELD OF THE INVENTION

This relates to the field of medical devices and more particularly to vascular guidewire introducer devices.

BACKGROUND OF THE INVENTION

Generally, to insert a catheter into a blood vessel, the vessel is identified by aspiration with a long hollow needle in accordance with the well-known Seldinger technique. In its simplest application, a needle, with a syringe attached, is introduced into the patient. When blood enters the syringe, it provides visual indication that the vessel has been found; the syringe is then disconnected from the needle and a thin guidewire is then introduced into the needle and into the interior of the vessel. The introducer needle is then removed from the patient and slid over the guidewire proximal end, leaving the distal end portion of the guidewire that has been inserted into the vessel within the vessel and the opposing end of the guidewire projecting beyond the surface of the skin of the patient. After which, the catheter is directed over the guidewire, either directly or using a dilator or the like.

During the procedure, when the syringe is removed from the introducer needle, bleeding can occur from the needle and onto the operative field, or air can be aspirated into the vessel if the patient inspires while the needle is not sealed prior to and during introduction of the guidewire into the needle. Blood on the operative field exposes the caregivers to contamination with blood-borne pathogens, and intravascular air can result in vascular occlusion and injury or death. Currently this is controlled by the interventionist by putting their finger tip on the needle hub.

SUMMARY OF THE INVENTION

In at least one aspect, the present invention provides a compressible section between the rigid needle and the hub. Once the vessel is entered as determined by blood entering the syringe, the compressible section of the introducer needle is occluded by compressing the section with the thumb and a finger. Neither blood nor air can pass. Since the compressible section is in a flattened area it is easier to hold the needle while the syringe is unscrewed. The operator then can begin threading a guidewire down the device which is now easier to enter because blood is not coming out of the hub thus obscuring the lumen. Compression is then released while the guidewire is passed with the guidewire now partially occluding blood or air passage.

In at least one embodiment, the present invention provides an introducer needle assembly including a hollow needle with a needle passage extending from a needle distal end to a needle proximal end. A hub extends from a hub distal end to a hub proximal end with the hub distal end secured to the needle proximal end. The hub includes a needle connector at the hub distal end and a device connector at the hub proximal end with a pair of spaced apart rails interconnecting the needle connector and the device connector with a hollow space defined therebetween. A first passage is defined from the needle connector through a first post extending proximally thereof and the first passage is in communication with the needle passage. A second passage extends from the device connector through a second post extending distally thereof. A compressible member having a tubular body defines a third passage extending between the ends thereof. The compressible member is secured on the first and second posts such that a continuous passage is defined through the second passage, the third passage, the first passage and the needle passage and the third passage has an inner diameter equal to or less than an inner diameter of the first passage.

In at least one embodiment, the hub of the introducer needle assembly has a generally wide, flat configuration extending in a plane extending between the side rails.

In at least one embodiment, opposed sides of the tubular body have indentations defined therein with a compression pad defined in the center of each indentation.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
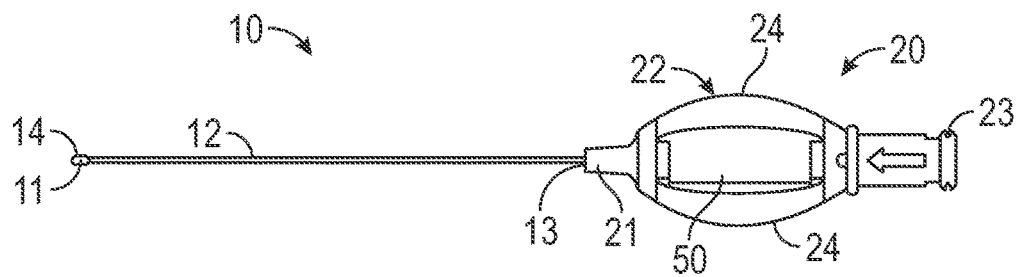
FIG. 1 is a plan view of an introducer needle assembly in accordance with an embodiment of the disclosure.

In the drawings, like numerals indicate like elements throughout. Certain terminology is used herein for convenience only and is not to be taken as a limitation on the present invention. The terms "distal" and "proximal" refer, respectively, to directions closer to and away from a patient's blood vessel. The following describes preferred embodiments of the present invention. However, it should be understood, based on this disclosure, that the invention is not limited by the preferred embodiments described herein.

Referring to FIGS. 1-7, an exemplary embodiment of an introducer needle assembly 10 in accordance with an embodiment of the invention will be described. The introducer needle assembly 10 generally comprises a hollow needle 12, a hub 20 and a compressible member 50. The hollow needle 12 extends from a distal end 11 to a proximal end 13 with a passage 14 extending therethrough. The proximal end 13 of the hollow needle 12 is connected with the distal end 21 of the hub 20.

Figure 2:
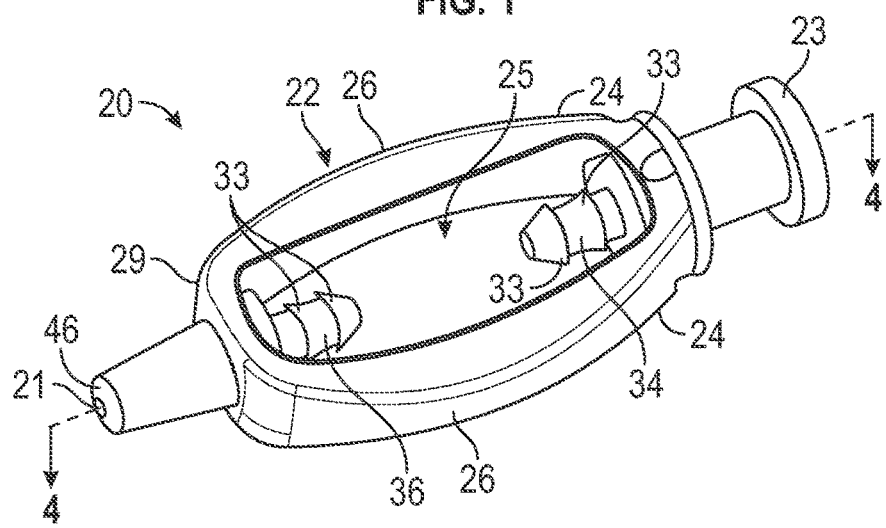
FIG. 2 is a perspective view of the hub of the introducer needle assembly of FIG. 1
Figure 3:
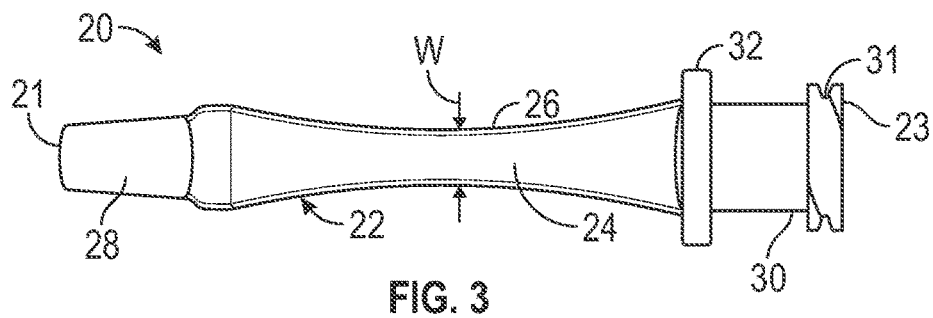
FIG. 3 is a side elevation view of the hub.
Figure 4:
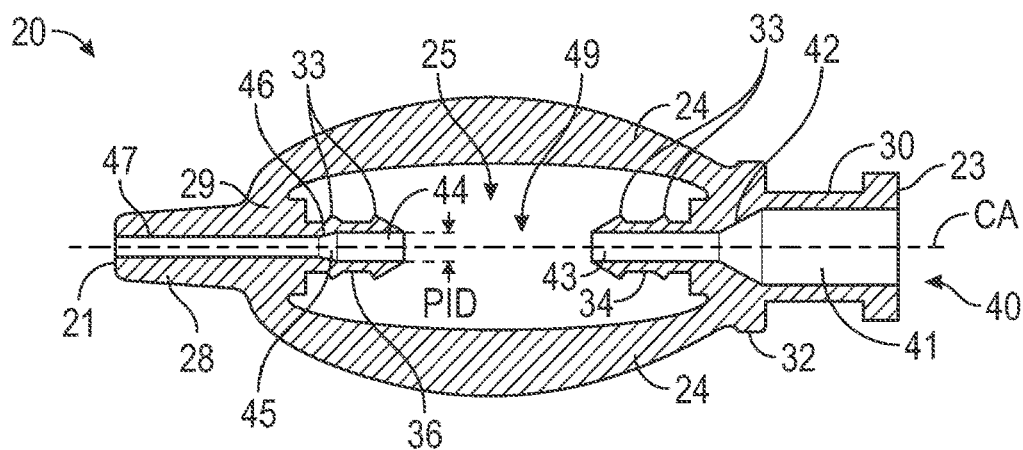
FIG. 4 is a cross-sectional view along the line 4-4 in FIG. 2.

Referring to FIGS. 2-4, the hub 20 includes a generally rigid body 22 extending from the distal end 21 to a proximal end 23 and includes a pair of side rails 24 extending between a needle connector 28 at the distal end 21 and a device connector 30 at the proximal end 23. In the illustrated embodiment, a bridge 29 interconnects the needle connector 28 with the side rails 24 and a shoulder 32 interconnects the device connector 30 with the side rails 24, although other configurations are contemplated. The needle connector 28 may be molded about the proximal end 13 of the hollow needle 12 or may be otherwise secured thereto. The device connector 30 includes a thread 31 or the like for engagement with the threads of a syringe or the like.

The configuration of the hub body 22 is preferably a generally flat, wide configuration such that the interventionist can easily grasp the hub 20 and prevent it from inadvertently rotating during the procedure, for example, while the syringe is twisted during detachment. Other configurations other than that specifically illustrated may also be utilized.

A hollow space 25 is defined between the side rails 24 for receipt of the compressible member 50 as will be described hereinafter. A proximal post 34 extends distally from the shoulder 32 and a distal post 36 extends proximally from the bridge 29. Each of the posts 34, 36 may include outwardly extending barbs 33 or the like to secure connection of the compressible member 50. A passage 40 extends along the central axis CA of the hub 20 from the proximal end 23 to the distal end 21, with an area of discontinuity 49 between the posts 34 and 36. As described below, upon assembly, a passage 54 through the compressible member 50 (see FIGS. 5-7) aligns with the passage 40 and eliminates the discontinuity such that a continuous passage extends through the hub 20 from the proximal end 23 to the distal end 21.

Figure 5:
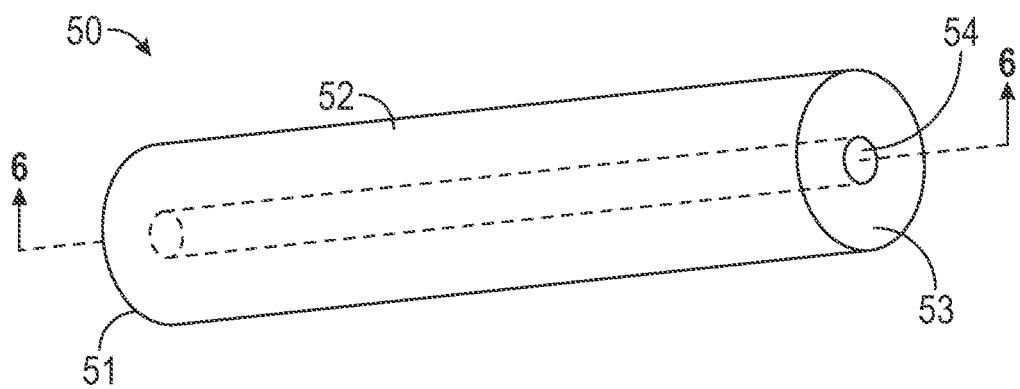
FIG. 5 is a perspective view of the compressible member of the introducer needle assembly of FIG. 1.
Figure 6:
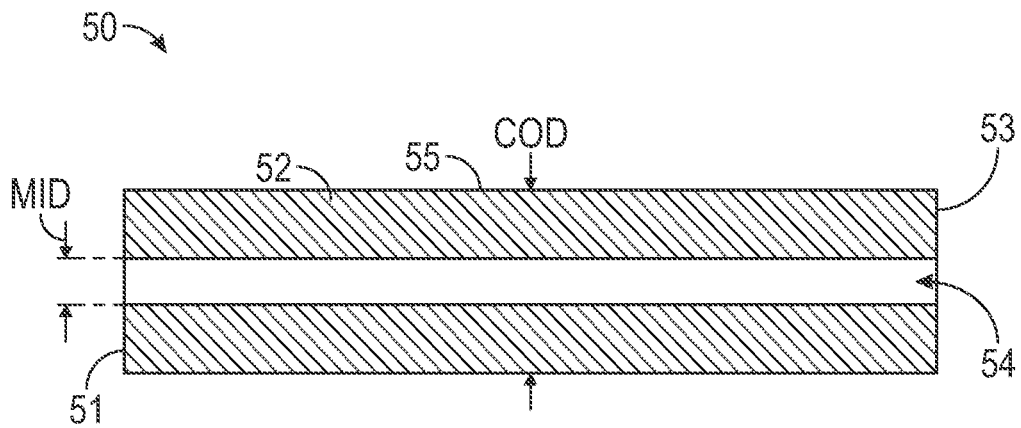
FIG. 6 is a cross-sectional view along the line 6-6 in FIG. 5.

Referring to FIGS. 5 and 6, an exemplary compressible member 50 will be described. The compressible member 50 has an elastic tubular body 52 extending from a distal end 51 to a proximal end 53. A passage 54 extends through the body 52 from the proximal end 53 to the distal end 51. The elastic body 52 has an outside diameter COD in a central region between the ends 51, 53 and the passage 54 defines an inner diameter MID. The distance between the outside diameter COD of the central region and the inner diameter MID defines a wall thickness in the central region, the area which will be compressed to occlude the passage 54. An alternative embodiment of the compressible member will be described hereinafter wherein the configuration of the elastic body 52 is such that the thickness to be compressed is reduced while still providing a sufficiently rigid structure and reliable compression area.

Figure 7:
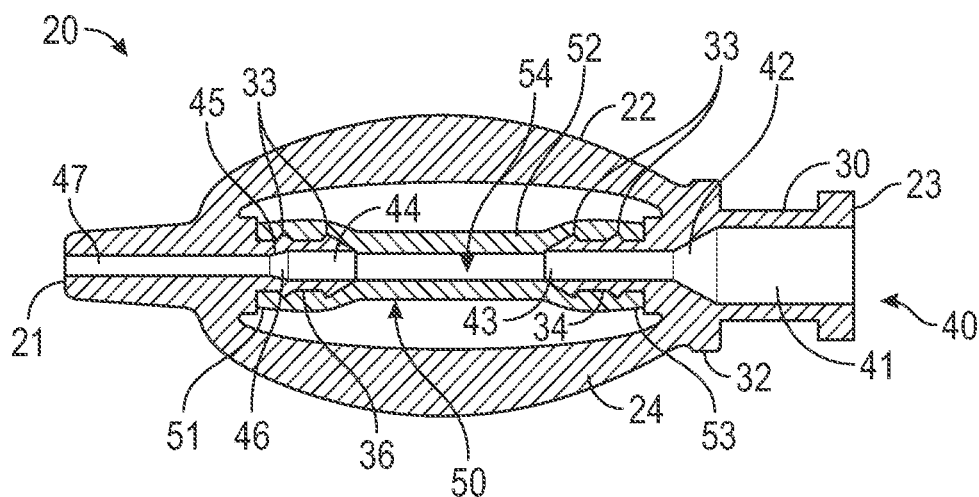
FIG. 7 is a cross-sectional of the hub and compressible member.
Figure 8:
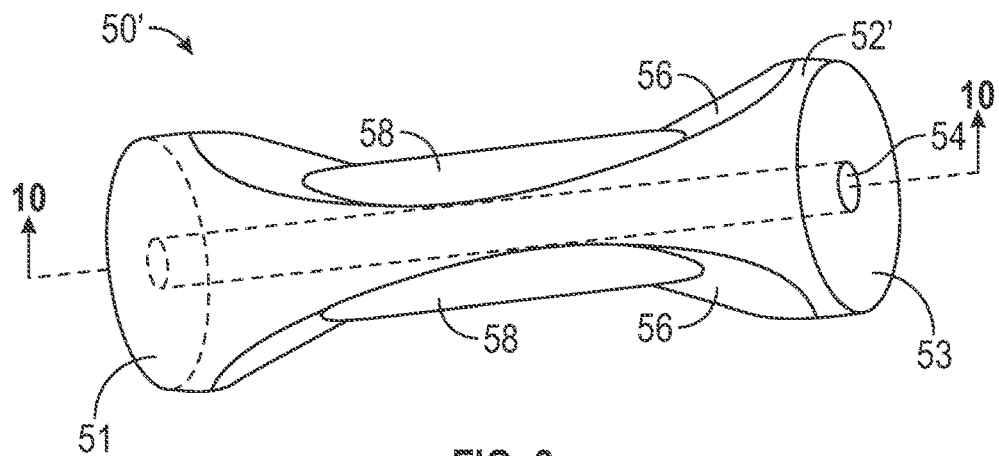
FIG. 8 is a perspective view of another exemplary compressible member in accordance with an embodiment of the disclosure.
Figure 9:
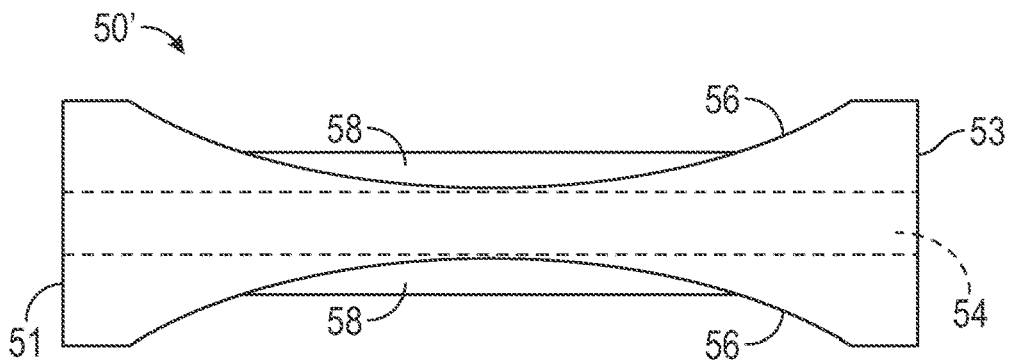
FIG. 9 is a side elevation view of the compressible member of FIG. 8.

With reference to FIG. 7, upon assembly, the proximal end 53 of the compressible member 50 is positioned over the proximal post 34 such that the post 34 is received in the passage 54. Likewise, the distal end 51 of the compressible member 50 is positioned over the distal post 36 such that the post 36 is received in the passage 54. The barbs 33 on each of the posts 34, 36 engage the compressible member 50 such that the ends 51, 53 thereof are retained on the posts 34, 36. Other securement arrangements may alternatively be utilized. With the compressible member 50 secured to the posts 34, 36, the passage 54 aligns with the passage 40 and a continuous passage is defined through the hub 20 from the proximal end 23 to the distal end 21. As illustrated in FIG. 3, each side rail 24 has a narrow central portion 26 with a width W which is less than the outside diameter COD of the central region of the compressible member. As such, the central region of the compressible member 50 will extend above the central portion 26 of the side rails 24, whereby it may be easily accessed to compress and thereby occlude the passage 54.

In use, the introducer needle assembly 10 with a syringe or the like (not shown) attached to the device connector 30 is utilized to access a blood vessel in a manner similar to the prior technique. The distal end 11 of the hollow needle 12 is introduced into the patient. When blood enters the syringe, it provides visual indication that the vessel has been found. At this time the syringe may be removed. Removal of the syringe generally requires two actions, twisting off of the syringe and occlusion of the passage. The exemplary configuration of the hub 20 facilitates the two actions generally happening in a simultaneous, intuitive manner. As the interventionist grabs the side rails 24 of the hub 20, for example between the interventionist's thumb and pointer finger, to stabilize the hub 20 such that he syringe may be twisted relative thereto, the thumb and pointer finger naturally extend above and below the compressible member 50. As a holding force is applied to the hub 20, the force may naturally be applied to the central region 55 of the compressible member 50 to occlude the passage 54. With the passage 54 occluded, the syringe may be removed. As indicated, the two actions may naturally occur almost simultaneously. After the syringe is removed, a thin guidewire is then passed through the hub 20, introduced into the needle and into the interior of the vessel. The interventionist may ease some, if not all, of the compressive force as the guidewire is passed through the passage 54. With the guidewire properly positioned, the introducer needle assembly 10 may be removed and the catheter inserted over the guidewire.

With reference to FIGS. 4, 6 and 7, the illustrated passage 40 and the passage 54 will be further described. The passages 40 and 54 are preferably configured to assist guidance of a guidewire (not shown) through the hub 20 into the hollow needle 12. In the illustrated embodiment, a large bore 41 is defined in the device connector 30 such that a large opening is defined at the proximal end 23 of the hub 20 to easily receive the guidewire. The passage 40 includes a tapered bore 42 distally of the large bore 41 which transitions to a narrower bore 43 through the proximal post 34. A similarly sized bore 44 extends into the distal post 36 and has an inner diameter PID. The inner diameter MID of the compressible member passage 54 is equal to or slightly smaller than the inner diameter PID of the bore 44. In this way, when the compressible member 50 is secured on the post 36, the inside surface of the passage 54 will be slightly inside of or aligned with the inside surface of the bore 44, thereby defining a smooth transition without any interruptions which may catch the guidewire and make passage through the hub 20 more difficult. The inner diameter of the bore 43 is preferably equal to the inner diameter PID, but could be slightly larger or smaller since the guidewire will be moving from the bore 43 to the passage 54 and the chance of catching is reduced.

The illustrated passage 40 includes another tapered bore 45 distally of the bore 44 which transitions to a bore 46 at about the bridge 29. The bore 46 has an inner diameter which is approximately equal to the inner diameter of the hollow needle. The bore 47 in the needle connector 28 is slightly larger in diameter than the bore 46, with the difference corresponding to the thickness of the hollow needle 12 wall. With such a configuration, upon assembly of the needle 12 with the hub 20, a generally continuous surface is defined between the bore 46 and the inside surface of the needle bore 14.

It is noted that inner diameter PID of the bore 44 may be the same as the inner diameter of the bore 46 whereby the tapered bored 45 can be eliminated. By reducing the inner diameter PID of the bore 44, the inner diameter MID of the compressible member passage 54 will be correspondingly reduced. Such a reduction in diameter is advantageous in that it will reduce the available volume for blood or air passage and will also reduce the diameter which must be occluded; however, an overly narrow passage 54 through the compressible member 50 may make passage of the guidewire therethrough more difficult. The passage inner diameter MID is therefore selected to balance the ease of passing the guidewire through the passage 54 while also being able to reliably occlude the passage.

The compressible member 50 may be manufactured from various natural and synthetic biocompatible elastomeric materials. As an example, the compressible member 50 may be manufactured from silicone. The materials and the hardness thereof may be selected such that the compressible member 50 has sufficient rigidity that a guidewire may pass through the passage 54 with minimal interference, yet is sufficiently elastic that the member 50 may be compressed and the passage 54 reliably occluded.

Figure 10:
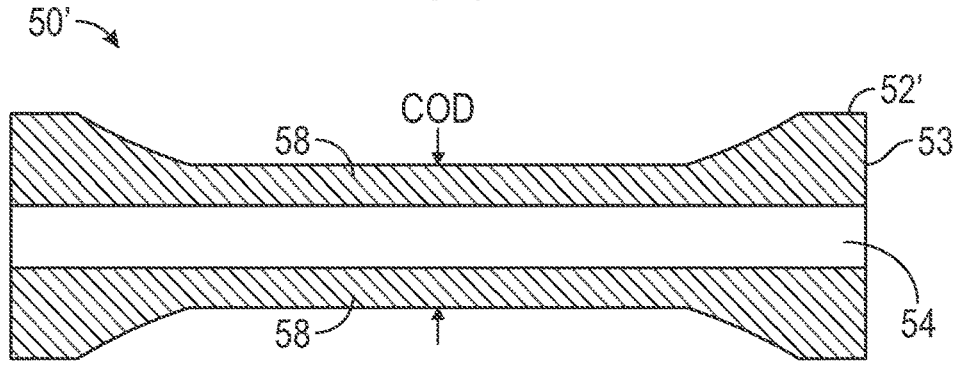
FIG. 10 is a cross-sectional view along the line 10-10 in FIG. 8.
Figure 11:
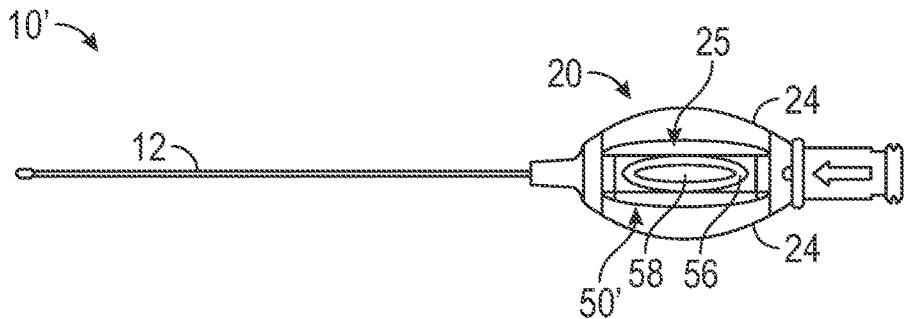
FIG. 11 is a plan view of an introducer needle assembly including the compressible member of FIG. 8.

Referring to FIGS. 8-11, an introducer needle assembly 10' with an alternative compressible member 50' will be described. The introducer assembly 10' includes a hollow needle 12 and hub 20 the same as in the previously described embodiment. The compressible member 50' is similar to the previous embodiment and includes an elastic, tubular body 52' extending from a distal end 51 to a proximal end 53. As in the previous embodiment, a passage 54 extends through the body 52 from the proximal end 53 to the distal end 51. In the present embodiment, opposed sides of the tubular body 52' have indentations 56 defined therein with a compression pad 58 defined in the center of each indentation 56. The indentations 56 and compression pads 58 define clear alignment points for the interventionist's fingers. As illustrated in FIG. 11, the compression pads 58 extend parallel with the plane of the side rails 24 and are easily accessible within the hollow space 25.

Furthermore, the indentations 56 reduce the amount of body material which must be compressed to occlude the passage 54; however, the compression pads 58 provide a sufficient thickness about the passage 54. The opposed compression pads 58 define opposed structures aligned with the passage 54 that can be brought together to occlude the passage 54. Compressing of the compression pads 58 provides a directed occluding force without any force being wasted on compressing outer portions of the tubular body 52' as such are removed by the indentations 56. As illustrated in FIG. 10, the compressible member 50' maintains a significant central outer diameter COD about the passage 54. The central outer diameter COD is again preferably larger than the width W of the central portion 26 of the side rails 24 such that the compression pads 58 are easily accessible.

The indentations 56 and compression pads 58 may be defined by cutting away of the body 52'. Alternatively, the body 52' may be manufactured, for example, via molding, with the indentations 56 and compression pads 58 already formed therein. In all other respects, the introducer needle assembly 10' functions similarly to that described above.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed is:

1. A method of inserting a needle into a blood vessel comprising the steps of:
   providing an introducer needle assembly comprising
      the needle with a needle passage extending from a needle distal end to a needle proximal end,
      a hub extending from a hub distal end to a hub proximal end with the hub distal end secured to the needle proximal end, the hub including a needle connector at the hub distal end and a device connector at the hub proximal end with a pair of spaced apart rails interconnecting the needle connector and the device connector with a hollow space defined between the rails;
      a first passage extending proximally from the needle connector, the first passage in communication with the needle passage, and
      a second passage extending distally from the device connector; and
      a compressible member having a tubular body having a third passage extending between the ends of the compressible member, a continuous passage is defined through the second passage, the third passage, the first passage and the needle passage and wherein the third passage has an inner diameter equal to or less than an inner diameter at a proximal end of the first passage;
      wherein the tubular body has opposed sides with indentations that can be compressed to occlude the third passage to block fluid communication;
   inserting the needle into the blood vessel;
   compressing the compressible member to occlude the third passage after blood enters a syringe attached to the device connector;
   removing the syringe from the device connector; and
   inserting a guide wire through the second passage, the third passage, the first passage, and the needle passage, and into the blood vessel.

2. The method of claim 1 wherein the compressing utilizes opposed first and second fingers of an interventionist with the opposed first and second fingers extending across at least one of the rails of the pair of spaced apart rails and the compressible member.

3. The method of claim 2 wherein the removing includes unscrewing the syringe from the device connector and a position of the opposed first and second fingers of the interventionist relative to the pair of spaced apart rails prevents rotation of the hub during unscrewing.

4. The method of claim 1 wherein the compressing and the removing are performed substantially simultaneously.

5. The method of claim 1 wherein the first passage is defined from the needle connector through a first post and the second passage extends from the device connector through a second post, and wherein the compressible member is secured on the first post and the second post.

6. The method of claim 5 wherein the first post and the second post each include at least one outwardly extending barb.

7. The method of claim 5 wherein the second passage includes a large opening at the proximal end of the hub and tapers to a narrower bore through the second post.

8. The method of claim 7 wherein the narrower bore has an inside diameter approximately equal to the inner diameter at the proximal end of the first passage.

9. The method of claim 1 wherein the hub has a generally wide, flat configuration extending in a plane between the pair of spaced apart rails.

10. The method of claim 1 wherein a compression pad is defined in the center of each indentation of the indentations and wherein compressing the compression pad defined in the center of each indentation of the indentations provides a directed occluding force without wasting any force on compressing outer portions of the tubular body.

11. The method of claim 10 wherein the compression pad defined in the center of each indentation of the indentations extend parallel with a plane between the pair of spaced apart rails.

12. The method of claim 1 wherein the compression pad defined in the center of each indentation of the indentations define an outer diameter which is larger than a width of a central portion of each rail.

13. The method of claim 1 wherein the compressible member defines a central outer diameter which is larger than a width of a central portion of each rail.

14. The method of claim 1 wherein the hub has a generally rigid body.

15. The method of claim 1 wherein the compressible member is manufactured from an elastic material.

16. The method of claim 1 wherein the device connector includes at least one external thread.

17. The method of claim 1 wherein the inner diameter at the proximal end of the first passage is approximately equal to an inner diameter of the needle passage.

18. The method of claim 1 wherein the inner diameter at the proximal end of the first passage is larger than an inner diameter of the needle passage and the first passage includes a tapered portion distal of the proximal end of the first passage.

* * * * *